US008748414B2

(12) United States Patent
Couvreur et al.

(10) Patent No.: US 8,748,414 B2
(45) Date of Patent: Jun. 10, 2014

(54) STATIN NANOPARTICLES

(76) Inventors: Patrick Couvreur, Villebon-sur-yvette (FR); Didier Desmaele, Fresnes (FR); Fat'ma Zouhiri, Chatenay-malabry (FR); Reddy Harivardhan Lakkireddy, Malakoff (FR)

( * ) Notice: Subject to any disclaimer, the term of this patent is extended or adjusted under 35 U.S.C. 154(b) by 251 days.

(21) Appl. No.: 13/126,752

(22) PCT Filed: Oct. 28, 2009

(86) PCT No.: PCT/IB2009/054781
§ 371 (c)(1),
(2), (4) Date: Jul. 19, 2011

(87) PCT Pub. No.: WO2010/049900
PCT Pub. Date: May 6, 2010

(65) Prior Publication Data
US 2011/0269830 A1 Nov. 3, 2011

(30) Foreign Application Priority Data

Oct. 29, 2008 (FR) ...................................... 08 57356

(51) Int. Cl.
A61K 31/047 (2006.01)
A61K 45/06 (2006.01)
A61K 31/196 (2006.01)

(52) U.S. Cl.
USPC ............ 514/167; 514/171; 514/567; 514/738

(58) Field of Classification Search
None
See application file for complete search history.

(56) References Cited

U.S. PATENT DOCUMENTS

| | | | |
|---|---|---|---|
| 6,726,911 B1 | 4/2004 | Julich et al. | |
| 7,704,972 B2 | 4/2010 | Couvreur et al. | |
| 7,879,361 B2 | 2/2011 | Sung et al. | |
| 8,044,034 B2 | 10/2011 | Couvreur et al. | |
| 2006/0013882 A1 | 1/2006 | Kohn et al. | |
| 2010/0305030 A1 | 12/2010 | Couvreur et al. | |
| 2011/0184053 A1 | 7/2011 | Couvreur et al. | |
| 2011/0269731 A1 | 11/2011 | Couvreur et al. | |

FOREIGN PATENT DOCUMENTS

| | | |
|---|---|---|
| GB | 2073193 | 10/1981 |
| WO | WO 95/24893 | 9/1995 |
| WO | WO 97/20835 | 6/1997 |
| WO | WO 00/53207 A1 | 9/2000 |
| WO | WO 02/053131 | 7/2002 |
| WO | WO 03/103640 | 12/2003 |
| WO | WO 2004/100888 A1 | 11/2004 |
| WO | WO 2005/110407 A1 | 11/2005 |
| WO | WO 2006/090029 A1 | 8/2006 |
| WO | WO 2008/033278 A1 | 3/2008 |
| WO | WO 2009/150344 A1 | 12/2009 |
| WO | WO 2010/049899 A1 | 10/2010 |

OTHER PUBLICATIONS

Bhatt et al. in Angewandte Chemie 117(43), 7237-7240 (2005).*
Aromaticity in The Virtual Textbook of Organic Chemistry (www2. chemistry.msu.edu/faculty/ reusch/virttxtjml/intro1.htm) (retrieved from the internet Sep. 30, 2013).*
Couvreur et al. in Nano Letters 6(11), 2544-2548 (2006).*
Armitage, "The Safety of Statins of Clinical Practice," The Lancet, vol. 370, 2007, pp. 1781-1790.
Author Affiliations, "Reduction in Incidence of Coronary Heart Disease," Journal of American Medical Association, vol. 251, No. 3, 1984, pp. 351-374.
Balland et al., "Intracellular Distribution of Ampicillin in Murine Macrophages Infected with *Salmonella typhimurium* and Treated with (3H) Ampicillin-Loaded Nanoparticles," The Journal of Antimicrobial Chemotherapy,1996, vol. 37, No. 1, pp. 105-115.
Bhatt et al., "Accumulation of an E, E, E-Triene by Monensin-Producing Polyketide Synthase When Oxidative Cyclization is Blocked," Angewandte Chemie, vol. 117, No. 43, 2005, pp. 7237-7240.
Couvreur et al., "Squalenoyl Nanomedicines as Potential Therapeutics," Nano Letters, 2006, vol. 6, No. 11, pp. 2544-2548.
Corcos et al., "Les Statines: Une Aide Realiste Dans La Prevention et le Traitement du Cancer," Medecine Therapeutique, vol. 13 Jan. 2007, pp. 22.
Date et al., "Design and Evaluation of Self-Nanoemulsifying Drug Delivery Systems for Cefpodoxime Proxetil," International Journal of Pharmaceutics, vol. 329, No. 1-2, 2007, pp. 166-172.
Dixit et al., "Formulation and in Vivo evaluation of Self-Nanoemulsifying Granules for Oral Delivery of a Combination of Ezetimibe and Simvastatin," Drug Development and Industrial Pharmacy, vol. 34, No. 12, 2008, pp. 1285-1296.
Du et al., "Preparation of .Alpha.—Phosphono Lactams Via Electophilic Phosphorus Reagents: An Application in the Synthesis of Lactam-Based Farnesyl Transferase Inhibitors," Journal of Organic Chemistry, 2002, vol. 67, No. 16, pp. 5709-5717.
Ebright, et al., "Incorporation of an EDTA-Metal Complex at a Rationally Selected Site within a Protein: Application to EDTA-Iron DNA Affinity Cleaving with Catabolite Gene Activator Protein (CAP) and Cro", Biochemistry, 1992, pp. 10664-10670, 31.
Far, "The activity of siRNA in mammalian cells is related to structural target accessibility: a comparison with antisense oligonucleotides," Nucl. Acids Res., 2003. pp. 4417-4424, 31(15).
Fessi et al., "Nanocapsule Formation by Interfacial Polymer Deposition Following Solvent Displacement," International Journal of Pharmaceutics, vol. 55, 1989, No. 1, pp. R1-R4.
File Registry, RN. 291542-70-6, Sep. 28, 2000.
File Registry, RN. 291542-71-7, Sep. 28, 2000.
File Registry, RN. 291542-72-8, Sep. 28, 2000.
Filleur, et al., "SiRNA-mediated Inhibition of Vascular Endothelial Growth Factor Severely Limits Tumor Resistance to Antiangiogenic Thrombospondin-1 and Slows Tumor Vascularization and Growth," Cancer Research, 2003, pp. 3919-3922, 63.

(Continued)

*Primary Examiner* — Dennis Heyer
(74) *Attorney, Agent, or Firm* — Jones Robb PLLC

(57) ABSTRACT

The present invention relates to a complex made up of at least one molecule of statin or a derivative thereof, covalently bonded to at least one hydrocarbon radical including at least 18 carbon atoms and containing at least one 2-methyl-buta-2-ene unit, to nanoparticles of such a complex, and to a method for preparing same, said complex and/or said nanoparticles optionally being in the form of a lyophilizate. The present invention also relates to a pharmaceutical composition including at least one complex and/or nanoparticles such as previously defined. The invention finally relates to said complex and/or to said nanoparticles for the treatment and/or prevention of hyperlipemia and hypercholesterolemia.

17 Claims, No Drawings

(56) References Cited

OTHER PUBLICATIONS

French Preliminary Search Report and French Written Opinion of French Application No. 08 53205, dated Dec. 2, 2008, which corresponds to International Search Report and Written Opinion of International Application No. PCT/FR2009/050887, for which an English language translation is included.

French Preliminary Search Report and French Written Opinion of French Application No. 08 57356, dated Oct. 29, 2008, which corresponds to International Search Report and Written Opinion of International Application No. PCT/IB2009/054781, for which an English language translation is included.

French Preliminary Search Report of French Application No. 08 57355, dated Oct. 29, 2008, which corresponds to International Search Report of International Application No. PCT/IB2009/054780, for which an English language translation is included.

French Written Opinion of French Application No. 08 57355.

Gnaccarini, et al., "Site-Specific Cleavage of RNA by a Metal-Free Artificial Nuclease Attached to Antisense Oligonucleotides," J. Am. Chem. Soc., 2006, pp. 8063-8067, 128.

Gunasekera et al., "Five New Discodermolide Analogues from the Marine Sponge *Discodermia* Species," Journal of Natural Products, 2002, vol. 65, pp. 1643-1648.

Hakimelahi et al., "Design and Synthesis of a Cephalosporin-Retinoic Acid Prodrug Activated by a Monoclonal Antibody-Beta-Lactamase Conjugate," Bioorganic and Medicinal Chemistry, 2001, vol. 9, No. 8, pp. 2139-2147.

International Search Report of International Publication No. WO 2009/150344 (International Application No. PCT/FR2009/050887), dated Dec. 17, 2009.

Written Opinion of International Publication No. WO 2009/150344 (International Application No. PCT/FR2009/050887), dated Nov. 16, 2010.

International Search Report of International Publication No. WO 2010/049900 (International Application No. PCT/IB2009/054781), dated Oct. 28, 2009.

Written Opinion of International Publication No. WO 2010/049900 (International Application No. PCT/IB2009/054781), dated Apr. 29, 2011.

International Search Report of International Publication No. WO 2010/049899 (International Application No. PCT/IB2009/054780), dated May 5, 2010.

Written Opinion of International Publication No. WO 2010/049899 (International Application No. PCT/IB2009/054780), dated Apr. 29, 2011.

Kang et al., "Development of Self-Microemulsifying Drug Delivery Systems (SMEDDS) for Oral Bioavailability Enhancement of Simvastatin in Beagle Dogs," International Journal of Pharmaceutics, vol. 274, No. 1-2, 2004, pp. 65-73.

de Martimprey, et al., "siRNA nanoformulation against the Ret/PTC1 junction oncogene is efficient in an in vivo model of papillary thyroid carcinoma," Nucleic Acids Res., 2008, pp. 1-13, 36(1).

Martin, et al., "Multiplexing siRNAs to compress RNAi-based screen size in human cells", 2007, pp. 1-8, 35(8).

Pala et al., "Terpene Compounds as Drugs," Arzneimittel-Forschung, Jan. 1, 1970, vol. 20, No. 1, pp. 62-68.

Pille, et al., Anti-RhoA and anti-RhoC siRNAs inhibit the proliferation and invasiveness of MDA-MB-231 breast cancer cells in vitro and in vivo, Mol. Ther., 2005, pp. 267-254, 11(2).

Reddy, et al., "A New Nanomedicine of Gemcitabine Displays enhanced Anticancer Activity in Sensitive and Resistant Leukemia Types," J. of Controlled Release, 2007, pp. 20-27, 124(1-2).

Relas et al., Fate of intravenously Administered Squalene and Plant Sterols in Human Subjects,: J. Lipid Research vol. 42, 2001, pp. 988.

Sengle, et al., "Synthesis, Incorporation Efficiency, and Stability of Disulfide Bridged Functional Groups at RNA 5'-Ends," Bioorganic & Med. Chem., 2000, pp. 1317-1329, 8.

Sheehan et al., "In Vitro Biological Activities of 6-Isosteric Penicillins and 7-Isosteric Cephalosporins," Journal of Antibiotics, 1984, vol. 37, No. 11, pp. 1441-1448.

Strandberg et al., "Metabolic Variables of Cholesterol During Squaline Feeding in Humans: Comparison with Cholestyramine Treatment," J. Lipid Research, vol. 31, 1990, pp. 1637-1643.

Suresh et al., "Preparation, Characterization, and In Vitro and In Vivo Evaluation of Lovastatin Solid Lipid Nanoparticles," AAPS PharmaSciTech, vol. 8, No. 1, 2007, pp. E162-E170.

Turos et al., "Antibiotic-Conjugated Polyacrylate Nanoparticles: New Opportunities for Development of Anti-MRSA Agents," Bioorganic & Medicinal Chemistry Letters, 2006, vol. 17, No. 1 pp. 53-56.

Turos et al., "Penicillin-Bound Polyacrylate Nanoparticles: Restoring the Activity of Beta-Lactam Antibiotics Against MRSA," Bioorganic & Medicinal Chemistry Letters, 2007, vol. 17, No. 12, pp. 3468-3472.

\* cited by examiner

STATIN NANOPARTICLES

This is a national stage application of PCT/IB2009/054781, filed internationally on Oct. 28, 2009, which claims priority to French Application No. 0857356, filed on Oct. 29, 2008.

The present invention aims to propose novel statin derivatives, in particular in a water-dispersible nanoparticulate form, compositions containing the same and therapeutic uses thereof.

Statins belong to the therapeutic class of hypocholesterolemic agents. They in particular lower LDL-cholesterol (low density lipoprotein cholesterol) and are, in this respect, particularly useful for treating or preventing certain cardiovascular diseases (*Journal of the American Medical Association*, 251, No. 3, 351-374 (1984)). This is because a large number of medical studies have revealed that the LDL-cholesterol dosage correlates best with the occurrence of cardiovascular events. In addition, LDL-cholesterol represents the type of lipids most responsible for the formation of atheroma plaques.

More specifically, statins reduce cholesterol biosynthesis in the liver by inhibiting the HMG-CoA reductase enzyme which controls the limiting step of cholesterol synthesis via the mevalonate pathway by converting 3-hydroxy-3-methyl-glutaryl-coenzyme A to mevalonic acid, a precursor of sterols. The use of statins is recommended if the LDL-cholesterol level exceeds 2.4 mmol/l in patients with coronary disease.

The treatment of cardiovascular diseases with drugs has thus been drastically changed by the appearance of statins, the effect on which on lowering the blood cholesterol level is often spectacular. Specifically, statins can reduce the total cholesterol concentration by 20 to 50%, the LDL-cholesterol concentration by 25 to 60% and the triglyceride concentration by 15 to 30%.

However, the contra-indications and side effects of statins are often serious and can, for example, manifest themselves through hypersensitivity to one of the constituents of the medicament, myopathy, which will sometimes result in severe kidney failure, progressive liver disease and/or prolonged elevation of transaminases (Armitage J., Lancet 2007; 370: 1781-1790). These effects are in particular caused by inadequate tissue and/or cell distribution.

It is therefore necessary to adjust the dose and mode of administration of statins as correctly as possible.

In the pharmaceutical industry, improving the bioavailability of active ingredients, intended to be administered orally, is a major preoccupation for specialists in galenics.

In particular, the formulation of statins, molecules which are generally lipophilic, poses real problems owing mainly to their low solubility in aqueous liquid pharmaceutical excipients, to their propensity to precipitate or recrystallize in aqueous solution and to their low solubility in the fluids of the gastrointestinal tract from which they must be absorbed.

The bioavailability of an active ingredient also depends on its concentration in the gastrointestinal fluid, said concentration itself being dependent on the release of the active ingredient. In particular, the more lipophilic an active ingredient is, the less tendency it has to migrate in gastrointestinal fluids.

In order to increase the bioavailability of lipophilic active ingredients, it has been envisioned, in WO 95/24893, to formulate them using digestible oils and hydrophilic and lipophilic surfactants. This type of formulation makes it possible to maintain the active ingredient in solution while it passes through the digestive tract, until its intestinal absorption.

The digestion of the oily ingredients of formulations of this type often has the advantage of solubilizing the active ingredient in mixed micelles consisting of bile salts and of products of lipolysis of the triglycerides of the digestible oil used.

However, the presence of surfactants can inhibit lipolysis, which requires prior in vitro evaluation of the digestibility of the oils for a given formulation. Furthermore, the amounts of digestible oils that it is sometimes necessary to use in order to avoid recrystallization of the active ingredient in vivo are too great to allow the manufacture of a marketable capsule.

The present invention in fact aims to overcome the abovementioned drawbacks and to provide formulations suitable for statins.

The inventors of the present invention have demonstrated that it is found to be possible to formulate statins in the form of nanoparticles in suspension in an aqueous medium and of small sizes, in particular compatibles with administration by injection or oral administration, with the proviso that they are covalently coupled to at least one hydrocarbon-based radical of squalene nature.

Thus, according to a first aspect, the present invention relates to a complex made up of at least one molecule of statin or a derivative thereof, covalently coupled to at least one hydrocarbon-based radical comprising at least 18 carbon atoms and containing at least one unit represented by the formula which follows:

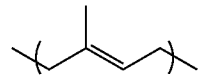

also known as 2-methylbut-2-ene.

According to another subject, the invention is directed toward a complex as defined above, in which the hydrocarbon-based compound comprises from 18 to 40 carbon atoms, preferably from 18 to 32 carbon atoms.

Advantageously, the two entities forming the complex defined above are coupled by means of a covalent bond of ester, ether, thioether, disulfide, phosphate or amide type, and preferably ester type.

Another subject of the present invention is directed toward nanoparticles of a complex as described above.

Admittedly, WO 2006/090029 and Couvreur et al., Nano Lett. 2006, 6, pp. 2544-2548 already describe the ability of a molecule containing at least one hydrocarbon-based radical as defined above, such as, for example squalene, to spontaneously form nanoparticles of about one hundred nanometers in an aqueous medium, when it is covalently coupled to a nucleoside derivative such as gemcitabine. However, for obvious reasons, gemcitabine is very different than the derivatives under consideration according to the invention.

It is also known that the administration of squalene, as such, results in its concentration, after oral or intravenous administration, in LDLs and VLDLs (very low density lipoproteins) (Strandberg et al., J Lipid Research, 31, 1637, 1999 and H. Relas et al., J Lipid Research, 42, 988, 2001).

As indicated above, the formulation of the therapeutic active agents under consideration according to the present invention, in the form of nanoparticles in accordance with the present invention, constitutes an advantageous alternative with regard to the formulations that already exist, in several respects.

First of all, the nanoparticulate form of statins advantageously makes it possible to improve the tissue and/or cell distribution, making it possible in particular to do away with the side effects of statins and thus adjust the administration modes and doses as appropriately as possible.

Advantageously, the mean size of these nanoparticles ranges from 30 to 500 nm, in particular from 50 to 250 nm, or even from 100 to 400 nm.

The present invention also relates to a method for preparing said nanoparticles, comprising at least the dispersion of the complex according to the present invention, in at least one organic solvent, at a concentration sufficient to obtain, when the resulting mixture is added, with stirring, to an aqueous phase, the instantaneous formation of nanoparticles of said complex in suspension in said aqueous phase, and, where appropriate, the isolation of said nanoparticles.

Advantageously, said method may also comprise a lyophilization step, particularly suitable for being able to formulate a solid form.

Thus, the present invention also relates to a lyophilisate comprising at least one complex and/or at least nanoparticles as described above.

According to another subject, the present invention is directed toward a complex and/or nanoparticles as defined above, optionally in the form of a lyophilisate as defined above, for preparing a pharmaceutical composition intended for the treatment and/or prevention of hyperlipemia, hypercholesterolemia, and in particular intended for the treatment and/or prevention of cardiovascular diseases, obesity, dyslipidemia and/or the prevention of a cardiovascular event.

In other words, a subject of the present invention is a complex and/or nanoparticles, optionally in the form of a lyophilisate, as defined according to the present invention, for the treatment and/or prevention of hyperlipemia, hypercholesterolemia, and in particular for the treatment and/or prevention of cardiovascular diseases, obesity, dyslipidemia and/or the prevention of a cardiovascular event.

The term "cardiovascular diseases" is intended to mean atherosclerosis (atheroma plaques), strokes or cerebral vascular events, heart events (infarction), lower limb arteritis, coronary diseases such as angina (or angina pectoris) or else infarctions such as myocardial infarction, ischemias, thrombosis and thromboembolic diseases, vessel diseases, such as aneurysms, obliterative arteriopathy of the lower limbs, acute aortic dissection, pulmonary arterial hypertension, thromboembolic diseases, heart attacks and congenital heart disease.

Hypercholesterolemia is generally the result of a disturbance of cholesterol biosynthesis and/or is caused by an abnormal circulating cholesterol level.

Moreover, the preventive role of statins on the occurrence of cancers of varied localizations (lung, prostate, breast, pancreatic, esophageal or colon cancers) has recently been demonstrated in Médecine Thérapeutique [Therapeutic Medicine], Corcos L. et al., Vol. 13, No. 1, 22-9, January-February 2007. Statins are also found to be useful as adjuvants for current anticancer therapies.

Thus, a subject of the present invention is also the complexes and/or nanoparticles according to the invention, optionally in the form of a lyophilisate, for the treatment and/or prevention of cancers, in particular lung, prostate, breast, pancreatic, esophageal or colon cancers, or as adjuvants for the current anticancer therapies.

The present invention also extends to a pharmaceutical composition, in particular a medicament, comprising at least one complex and/or nanoparticles, said complexes and/or nanoparticles being optionally in the form of a lyophilisate, as described above, in combination with at least one acceptable pharmaceutical vehicle.

The present invention is also directed toward said composition for use thereof as a medicament for the treatment and/or prevention of the abovementioned diseases and/or conditions.

Such a composition may prove to be most particularly useful as a medicament for the treatment and/or prevention of the abovementioned diseases and disorders in patients termed "at risk", i.e. in patients with high blood pressure and exhibiting other cardiovascular risk factors, such as smoking, being overweight, a family history of heart disease or diabetes, in particular type II diabetes. This is because the presence of such risk factors in a patient increases the risk of the occurrence of cardiovascular events in said patient.

Hydrocarbon-Based Compound or Radical Having a Squalene Structure

For the purposes of the present invention, a compound or radical having a squalene or squalenoyl structure is a compound or radical comprising at least one 2-methylbut-2-ene unit, as defined above.

More specifically, a hydrocarbon-based compound or radical having a squalene or squalenoyl structure comprises at least 18 carbon atoms and contains at least one 2-methylbut-2-ene unit, like a squalene radical.

It should be noted that, in the present invention, reference is made, as appropriate, to a "compound" or "radical" having a squalene or squalenoyl structure. The term "compound" is intended more specifically to define a compound having a squalene or squalenoyl structure, which, when it reacts with a molecule of active agent, forms a complex, whereas the term "radical" defines more specifically the squalene or squalenoyl part of the complex formed.

For the purpose of the present invention, a hydrocarbon-based radical having a squalene structure may be represented by the formula (I) which follows:

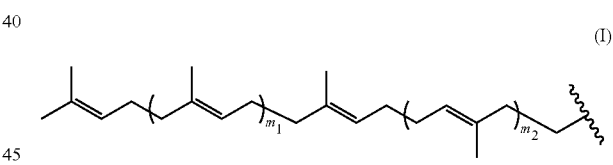

in which:

$m_1 = 1, 2, 3, 4, 5$ or $6$;

$m_2 = 0, 1, 2, 3, 4, 5$ or $6$; and

represents the bond toward the molecule of statin or a derivative thereof, it being understood that, when $m_2$ represents 0, then $m_1$ represents at least 2.

More specifically, when reference is made to the squalenoyl compound or a derivative thereof, the starting entity having served for the coupling, this compound or a derivative thereof may be represented by the compound of formula (Ia):

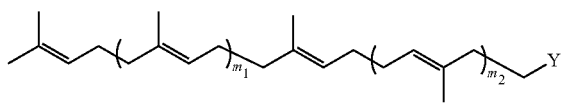

(Ia)

in which:

Y represents a hydrogen atom or an -L$_2$-X' group in which X' represents a function of alcohol, carboxylic acid, thiol, phosphate, amine, carboxamide or ketone type and L$_2$ represents a single covalent bond or a C$_1$-C$_4$ alkylene group; and m$_1$ and m$_2$ are as defined for the radical of formula (I).

The hydrocarbon-based radical comprises at least 18 carbon atoms, in particular from 18 to 40 carbon atoms and preferably from 18 to 32 carbon atoms.

More specifically, a compound that is of use for the formation of a complex according to the present invention is squalene (also known as spiracene or sirprene), which is an essential intermediate of cholesterol biosynthesis. Chemically, it is also known as (E)-2,6,10,15,19,23-hexamethyl-2,6,10,14,18,22-tetracosahexene having the formula which follows:

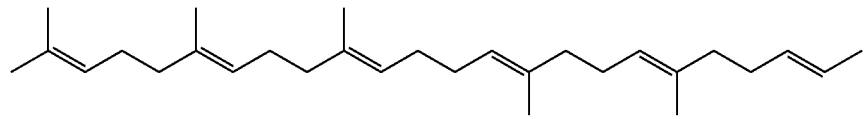 [SMILES: C/C=C/CC/C(C)=C/CC/C(C)=C/CC/C=C(\C)CC/C=C(\C)CCC=C(C)C]

According to one preferred embodiment of the invention, the squalene derivative present in a complex according to the present invention is a radical of formula (I) in which, m$_1$=1 and m$_2$=2.

Advantageously, said complex is a radical of formula (I) in which m$_1$=1 and m$_2$=3.

According to one preferred embodiment of the present invention, the squalene derivative present in a complex according to the present invention is a radical of formula (I') which follows, corresponding to a radical of formula (I) above in which m$_2$=0:

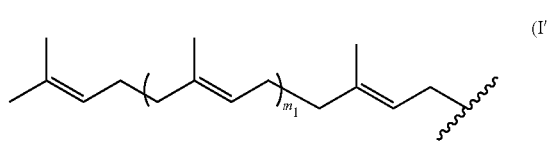

(I')

In this case, m$_1$=2, 3, 4, 5 or 6.

By way of illustration of hydrocarbon-based compounds capable of forming a complex according to the present invention, mention may more particularly be made of squalenic acid and derivatives thereof, such as 1,1',2-trisnorsqualenic acid, 1,1',2-trisnorsqualenamine, 1,1',2-trisnorsqualenol, 1,1',2-trisnorsqualenethiol, squalene acetic acid, squalenylethanol, squalenylethanethiol or squalenylethylamine.

A complex according to the present invention comprises at least one hydrocarbon-based radical represented by a radical of formula (I) as defined above.

In particular, a complex according to the present invention may contain at least one radical derived from a molecule of 1,1',2-trisnorsqualenic acid.

Alternatively, a complex according to the present invention comprises at least two hydrocarbon-based radicals as defined according to the present invention and in particular represented by the abovementioned compound of formula (I).

As noted by the inventors, a hydrocarbon-based compound as defined above spontaneously displays, when it is brought into contact with a polar medium and more particularly water, a compacted conformation.

Unexpectedly, the inventors have noted that this ability remains when such a radical is associated with, and in particular covalently bonded to, a molecule of statin or a derivative thereof. This results in the creation of a compacted architecture in the form of nanoparticles, in which there are at least partly a statin molecule entity and at least one hydrocarbon-based radical.

The statin molecule may in fact be only partly or be totally in the compacted state in the nanoparticles formed.

Generally, at least one abovementioned hydrocarbon-based radical is covalently bonded to a statin molecule. However, the number of molecules of hydrocarbon-based derivative capable of interacting with said molecule may be greater than 1.

Statin

Structurally, statins or derivatives thereof have in common a 4-hydroxy-6-oxo-2H-pyran system, which may also be in the form of dihydroxy acid which interacts with the active site of HMG-CoA reductase, an enzyme involved in cholesterol synthesis, and a lipophilic part which presents in particular as a polysubstituted hexahydronaphthalenic system, but may also be replaced with a polysubstituted heteroaromatic system, as in atorvastatin or fluvastatin.

The main known statins are: simvastatin, lovastatin, pravastatin, atorvastatin, fluvastatin and rosuvastatin.

These statins are generally lipophilic in nature (WO 02/053131). For example, simvastatin has a log P=4.68 and lovastatin a log P=4.04.

The lipophilicity of an active ingredient can be determined according to its partition coefficient (P) between octanol and water, which corresponds to the ratio of the concentration of the active ingredient in octanol (C$_{oct}$)/concentration of the active ingredient in water (C$_{water}$).

When the P ratio is greater than 1, this means that C$_{oct}$ is greater than C$_{water}$, and that, consequently, the active ingredient is lipophilic (log P>0). It can therefore be deduced therefrom that the higher the log P of an active ingredient, the more pronounced the lipophilic nature of said active ingredient.

More specifically, for the purposes of the present invention, the term "statin or a derivative thereof" is intended to mean a compound represented by formula (IIa), (IIb) or (IIc) which follows:

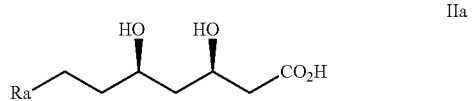

IIa

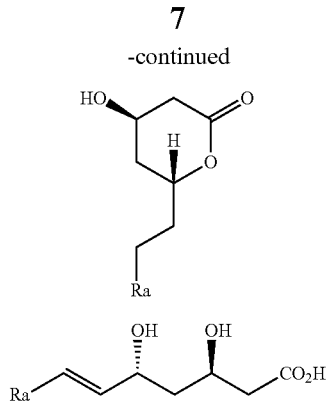

in which:

$R_a$ represents an aryl or heteroaryl group, optionally substituted with one or more R group(s);

R independently represents a hydroxyl group, a $C_1$-$C_6$ alkyl group, a $C_1$-$C_6$ alkoxy group, an —O—C(O)$C_1$-$C_6$ alkyl group, a phenyl, an —NR$_1$R$_2$ group, a —C(O)NR$_1$R$_2$ group or a —C(O)OR$_3$ group, said alkyl and phenyl groups being optionally substituted with one or more halogen atoms or with one or more hydroxyl groups;

$R_1$ and $R_2$ represent, independently of one another, a hydrogen atom, a $C_1$-$C_6$ alkyl group, an —SO$_2$—$C_1$-$C_6$ alkyl group or a phenyl, said $C_1$-$C_6$ alkyl and phenyl groups being optionally substituted with one or more halogen atoms or with one or more hydroxyl groups;

$R_3$ represents a hydrogen atom, or a $C_1$-$C_6$ alkyl optionally substituted with one or more halogen atoms or with one or more hydroxyl groups.

For the purpose of the present invention:

the term "a halogen atom" is intended to mean: a fluorine atom, a chlorine atom, a bromine atom or an iodine atom;

the term "a hydroxyl group" is intended to mean: an —OH group;

the term "an alkyl" is intended to mean: a linear or branched, saturated aliphatic group. By way of example, mention may be made of methyl, ethyl, propyl, isopropyl, butyl, isobutyl, sec-butyl and tert-butyl;

the term "an alkoxy" is intended to mean: an —O-alkyl radical where the alkyl group is as defined above, for example methoxy, ethoxy, propoxy, isopropoxy, butoxy, isobutoxy, sec-butoxy, tert-butoxy;

the term "an aryl group" is intended to mean: an aromatic group that may be partially unsaturated and monocyclic or bicyclic, comprising from 6 to 10 carbon atoms. By way of example of a monocycle, mention may be made of phenyl. By way of example of a bicycle, mention may be made of naphthyl, it being possible for said naphthyl to be partially unsaturated, such as 1,2,6,7,8,8a-hexahydronaphthyl;

the term "a heteroaryl group" is intended to mean: an abovementioned aryl group additionally comprising at least one heteroatom chosen from a nitrogen, a sulfur or an oxygen. By way of example of a monocycle, mention may be made of furanyl, thiophenyl, thienyl, pyrrolyl, thiazolyl, imidazolyl, pyrazolyl, isoxazolyl, thiadiazolyl, pyridinyl, pyrimidyl and pyruinyl. By way of example of a bicycle, mention may be made of indolyl, isoindolyl, indolizinyl, benzofuranyl, benzimidazolyl, quinolyl, isoquinolyl and phthalazyl.

The compounds of general formula (IIa), (IIb) or (IIc) may comprise one or more asymmetric carbons. They may therefore exist in the form of enantiomers or diastereoisomers. These enantiomers and diastereoisomers, and also mixtures thereof, including racemic mixtures, are part of the invention.

The compounds of formulae mentioned above may exist in the form of bases or of addition salts with acids. Such addition salts are part of the invention.

These salts are advantageously prepared with pharmaceutically acceptable acids, but the salts of other acids that are of use, for example, for purifying or separating the compounds of abovementioned formulae are also part of the invention.

The compounds of general formula (IIa), (IIb) or (IIc) may also be in the form of hydrates or of solvates, namely in the form of associations or combinations with one or more molecules of water or with a solvent. Such hydrates and solvates are also part of the invention.

Among the statins of formula (IIa) that are suitable for the present invention, mention may, for example, be made of pravastatin and atorvastatin.

Among the statins of formula (IIb) that are suitable for the present invention, mention may, for example, be made of simvastatin and lovastatin.

Among the statins of formula (IIc) suitable for the present invention, mention may, for example, be made of fluvastatin and rosuvastatin.

A statin most particularly suitable for implementing the present invention is represented by a compound of formula (IIa).

Advantageously, according to the present invention, simvastatin, lovastatin, pravastatin, atorvastatin, fluvastatin or rosuvastatin, and most particularly pravastatin, may be used in the complexes and/or nanoparticles according to the invention.

Hydrocarbon-Based Radical/Statin Complex

The conjugation of a statin molecule with a hydrocarbon-based derivative in accordance with the invention, and more particularly with 1,1',2-trisnorsqualenol, confers on the statin molecule physicochemical characteristics sufficient to give it an ability to form particles by nanoprecipitation, the size of said particles proving to be compatible with any mode of administration, in particular intravenous and oral.

For the purpose of the present invention, such a conjugation results in the formation of a complex or conjugate of statin/hydrocarbon-based radical according to the present invention, i.e. an entity comprising a radical derived from a statin molecule, covalently bonded to a hydrocarbon-based radical as defined above.

For the purpose of the present invention, the terms "complex" or "conjugate" will therefore be used without distinction to denote such an entity.

Thus, the present invention relates to a complex characterized in that it has the ability to organize spontaneously in the form of nanoparticles when it is in the presence of an aqueous medium.

The formation of the complex of statin/hydrocarbon-based radical according to the invention requires that the two entities of the complex bear functions capable of forming a covalent bond and/or a linker arm, as defined below. These functions may or may not be present on the two starting entities. If they are not present, the starting entity or entities will have to undergo a modification, prior to the coupling reaction.

More specifically, the hydrocarbon-based compound according to the invention generally bears a function capable of reacting with a function present on the statin molecule under consideration, so as to establish a covalent linkage between the two entities, for example of ester, ether, thioether, disulfide, phosphate or amide type, thus forming a covalent complex.

Advantageously, the function is an ester function. In this case, the hydrocarbon-based compound having a terpenic structure is 1,1',2-trisnorsqualenol or a derivative thereof, and in particular 1,1',2-trisnorsqualenyl bromoacetate.

According to one embodiment variant, the covalent linkage that exists between the two types of molecules can be represented by a spacer or alternatively a linker arm. Such an arm may in particular prove to be useful for increasing the force of the statin/hydrocarbon-based radical according to the invention interaction or else for facilitating the activation of the conjugate, after its administration, by the enzymes of the organism (esterases, cathepsins, for example) and thus allowing the controlled release of the statin molecule.

Such an arm in fact makes it possible to introduce, via each of the two ends of its backbone, the appropriate functions, i.e. functions respectively having the expected reactional affinity, one for the function present on the derivative having a hydrocarbon-based structure according to the invention and the other for the function present on the statin molecule under consideration.

It may also be envisaged that this linker arm additionally has in its backbone a labile function, which is subsequently suitable for separating the compound having a hydrocarbon-based structure from the statin molecule under consideration. It may, for example, be a peptide unit that can be recognized by an enzyme.

Units of linker arm type are well known to those skilled in the art and their use clearly falls within the competence thereof.

By way of representation of the linker arms that may be envisioned according to the invention, mention may in particular be made of the alkylene chains as defined above, (poly)amino acid units, polyol units, saccharide units, and polyethylene glycol (polyetheroxide) units.

For the purpose of the present invention:
the term "saccharide unit" is intended to mean a radical comprising at least one radical chosen from trioses (glyceraldehyde, dihydroxyacetone), tetroses (erythrose, threose, erythrulose), pentoses (arabinose, lyxose, ribose, deoxyribose, xylose, ribulose, xylulose), hexoses (allose, altrose, galactose, glucose, gulose, idose, mannose, talose, fructose, psicose, sorbose, tagatose), heptoses (mannoheptulose, sedoheptulose), octoses (octolose, 2-keto-3-deoxymannooctoriate), isonoses (sialose), and the term "(poly)amino acid unit" is intended to mean a unit having at least one unit:

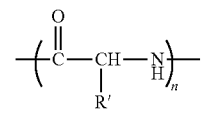

in which n is greater than or equal to 1, and R' represents a hydrogen atom, a $C_1$-$C_6$ alkyl group, optionally substituted with one or more hydroxyls, or a $C_1$-$C_6$ alkoxy.

Thus, for the purpose of the present invention, a "covalent linkage" preferably represents a covalent bond, in particular as specified above, but also covers a covalent linkage represented by a linker arm as defined above.

Thus, the covalent complex according to the present invention can be represented by the compound of formula (III) which follows:

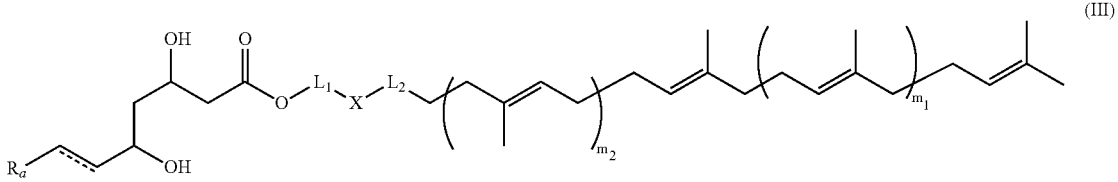

in which:
X represents a single covalent bond or a function of ester, ether, thioether, disulfide, phosphate or amide type;
$L_1$ and $L_2$ represent, independently of one another, a single covalent bond or a $C_1$-$C_4$ alkylene group; and
$R_a$ is as defined for the compound of formula (IIa), (IIb) or (IIc); and $m_1$ and $m_2$ are as defined above for the compound of formula (I); and
⁀ represents the optional presence of a center of unsaturation.

For the purpose of the present invention, the term "a $C_1$-$C_4$ alkylene group" is intended to mean a divalent alkyl group that may comprise from 1 to 4 carbon atoms. By way of example, mention may be made of methylene, propylene, isopropylene and butylene.

The present invention relates more particularly to a complex, represented by the compound of formula (IIIa) or (IIIb) which follows:

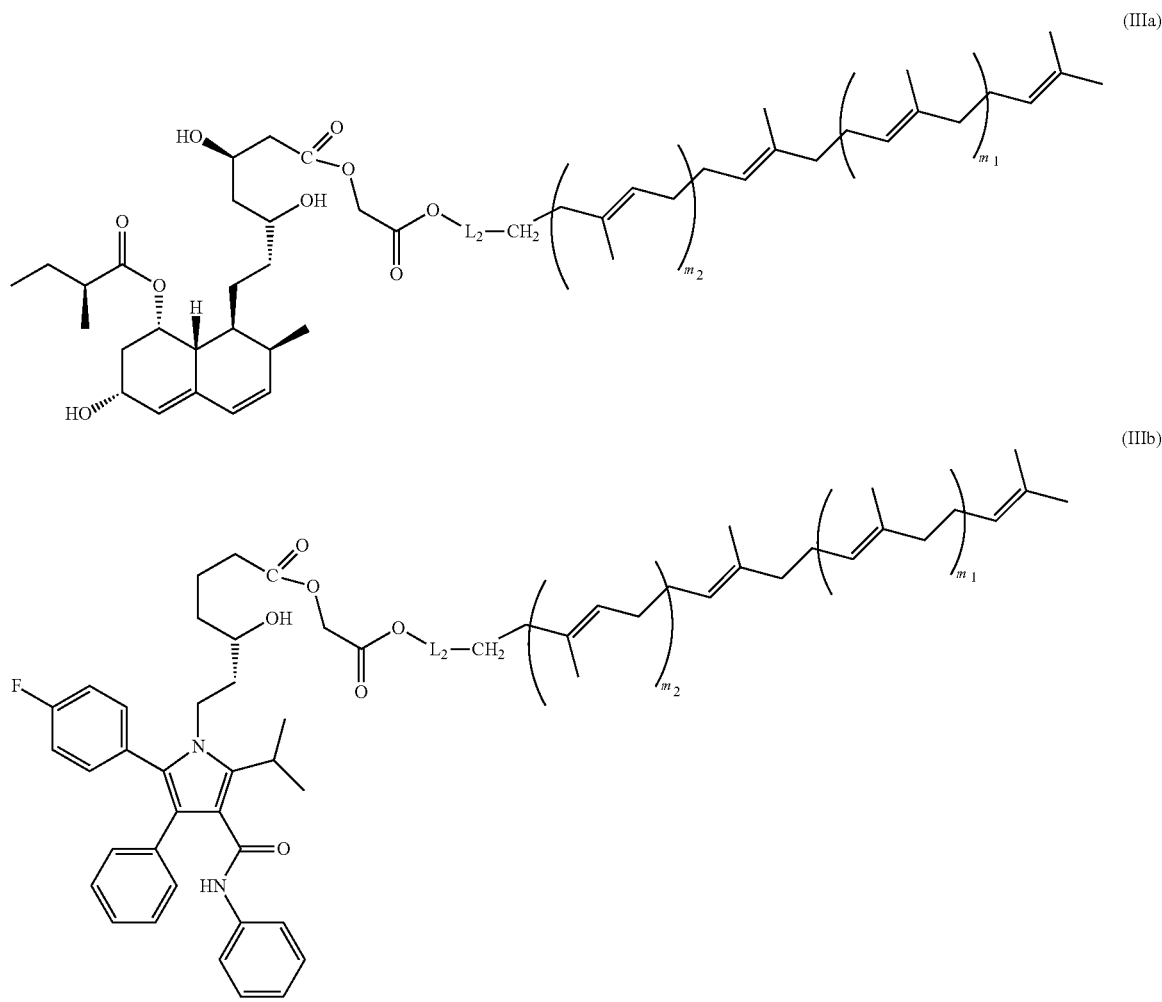

(IIIa)

(IIIb)

in which:
$m_1$ and $m_2$ are as defined for the compound of formula (I) and $L_2$ is as defined for the compound of formula (III).

In particular, a complex of formula (IIIa) or (IIIb), preferably the complex of formulae (IIIa), is used according to the present invention.

A subject of the present invention is therefore directed toward a complex in accordance with the invention, which may be represented by formula (III), (IIIa) or (IIIb), as defined above.

Method for Preparing the Complex

The reaction necessary for the establishment of at least one covalent bond between at least one statin molecule under consideration and at least one hydrocarbon-based radical in accordance with the present invention can be carried out according to standard conditions, and the implementation thereof is therefore clearly part of the knowledge of those skilled in the art.

More particularly, the bond between the statin and the hydrocarbon-based radical is produced by nucleophilic substitution with 1,1',2-trisnorsqualenyl bromoacetate. This reaction is generally carried out in solution in a polar solvent in the presence and with an excess of at least one hydrocarbon-based compound under consideration according to the present invention, relative to the statin molecule used according to the invention, for example in a proportion of two equivalents, according to the standard conditions required for interaction between the two specific functions borne by each of the two entities.

As indicated above, the establishment of the covalent bond between the two entities to be considered according to the invention requires, as appropriate, that each of the groups that must react bears functions capable of reacting with one another, for instance a carboxyl function with a hydroxyl function so as to form an ester bond or alternatively an amine function with a carboxyl function so as to form an amide bond.

Thus, if necessary, one of the two entities, on the one hand the statin molecule and, on the other hand the hydrocarbon-based compound, are modified prior to the coupling reaction in order to provide them with the appropriate function for conferring on them the reactivity necessary for the formation of a covalent bond between them. Preferably, each of the two molecules is modified in order to establish an amide or ester bond between them.

Preferably, a starting hydrocarbon-based compound for the synthesis of a complex according to the invention is a squalene derivative, for instance 1,1',2-trisnorsqualenol, as illustrated in step 1.1 of example 1.

Nanoparticles According to the Invention

As specified above, the covalent coupling of at least one statin molecule under consideration according to the invention with at least one hydrocarbon-based compound according to the invention is of a nature to give the statin molecule thus complexed an ability to become organized in a compacted form in a polar solvent medium, thus leading to the formation of nanoparticles.

In general, the nanoparticles thus obtained have a mean size ranging from 30 to 500 nm, in particular from 50 to 250 nm, or even from 100 to 400 nm, measured by light scattering using a Coulter® N4MD nanosizer from Coulter Electronics, Hialeah, USA.

A subject of the invention is directed toward nanoparticles in accordance with the invention, the mean size of which ranges from 30 to 500 nm, in particular from 50 to 250 nm, or even from 100 to 400 nm.

Another subject of the present invention relates to nanoparticles of 4-(N)-squalenoyl-6-epi-pravastatin. The obtaining of such nanoparticles is illustrated in example 2.

Advantageously, the nanoparticles according to the present invention, in particular in the form of a lyophilisate, are particularly advantageous for oral administration.

Method for Preparing the Nanoparticles

The formation of nanoparticles from the complex described above can be carried out according to conventional techniques insofar as they involve bringing a complex into contact with an aqueous medium under conditions suitable for its agglomeration in the form of nanoparticles. This may in particular involve methods referred to as nanoprecipitation or emulsion/solvent evaporation.

The nanoparticles according to the present invention may preferably be obtained in the following way.

Preliminarily, a statin/hydrocarbon-based compound complex is formed by coupling at least one hydrocarbon-based compound according to the invention to at least one statin molecule according to the invention, as described above.

Said complex obtained is then dispersed in at least one organic solvent (for example an alcohol such as ethanol, or acetone) at a concentration sufficient to obtain, when the resulting mixture is added, with stirring, and generally dropwise, to an aqueous phase, the instantaneous formation of nanoparticles according to the invention in suspension in said aqueous phase. Where appropriate, said nanoparticles are isolated according to techniques well known to those skilled in the art.

The reaction can generally be carried out at ambient temperature. Irrespective of its value, the reaction temperature should not affect the activity of the statin molecule under consideration. The method for preparing the nanoparticles according to the invention is particularly advantageous since it does not require the obligatory presence of surfactants, but this may nevertheless prove to be necessary in the case, for example, where pravastatin is used.

This property is particularly beneficial since a large number of surfactants do not prove to be compatible with an in vivo application.

However, it is understood that the use of surfactants, generally advantageously free of any toxicity, can be envisioned in the context of the invention. Surfactants of this type may, moreover, make it possible to obtain even smaller sizes during the formation of nanoparticles. By way of nonlimiting illustration of surfactants of this type which can be used in the present invention, mention may in particular be made of polyoxyethylene-polyoxypropylene copolymers, phospholipid derivatives and lipophilic derivatives of polyethylene glycol.

As a lipophilic derivative of polyethylene glycol, mention may, for example, be made of polyethylene glycol cholesterol and polyethylene glycol squalene. As examples of polyoxyethylene-polyoxypropylene block copolymers, mention may particularly be made of polyoxyethylene-polyoxypropylene-polyoxyethylene triblock copolymers, also known as Poloxamers®, Pluronics® or synperonics, and which are sold in particular by the company BASF.

Poloxamines, which are related to these families of copolymers, and which consist of hydrophobic segments (based on polyoxypropylene), hydrophilic segments (based on polyoxyethylene) and a central part deriving from the ethylenediamine unit, can also be used.

The nanoparticles according to the invention are of course capable of bearing, at the surface, a multitude of reactive functions, such as hydroxyl or amine functions, for example. It is therefore possible to envision attaching all sorts of molecules to these functions, in particular via covalent bonds.

By way of nonlimiting illustration of molecules of this type which are capable of being associated with nanoparticles, mention may in particular be made of molecules of label type, compounds capable of performing a targeting function, and also any compound that is capable of imparting particular pharmacokinetic characteristics thereto. With regard to the latter aspect, it may thus be envisioned to attach, at the surface of these nanoparticles, lipophilic derivatives of polyethylene glycol, for instance the polyethylene glycol/cholesterol conjugate, polyethylene glycol phosphatidylethanolamine, or better still polyethylene glycollsqualene. Specifically, considering the natural affinity of squalene residues for one another, the polyethylene glycol/squalene conjugate associates, in the case in point, with the nanoparticles according to the invention, and thus results in the formation of nanoparticles surface-coated with polyethylene glycol. Moreover, and as mentioned above, the polyethylene glycol/squalene conjugate advantageously acts, during the process of formation of the nanoparticles according to the invention, as a surfactant owing to its amphiphilic behavior and therefore stabilizes the colloidal solution, thus reducing the size of the nanoparticles formed. A surface coating based on such compounds, and in particular polyethylene glycol or the polyethylene glycol/cholesterol conjugate or the polyethylene glycol/squalene conjugate, is in fact advantageous for imparting increased vascular remanence owing to a significant reduction in uptake of nanoparticles by liver macrophages.

According to one advantageous embodiment, the nanoparticles according to the invention are formulated in the form of an aqueous dispersion.

According to another particular embodiment, this aqueous dispersion contains less than 5% by weight, or even less than 2% by weight, and more particularly is devoid of surfactant or the like, for instance polyethylene glycols, polyglycerol and derivatives thereof, such as the esters, for example.

According to another advantageous embodiment, this aqueous dispersion contains less than 5% by weight, or even less than 2% by weight of $C_2$ to $C_4$ alcohol, for instance ethanol.

Thus, the formulation, in an aqueous medium, of the statin under consideration by means of squalenic acid in the form of water-dispersible nanoparticles advantageously makes it possible to obtain a suspension of nanoparticles without any additive other than the 5% dextrose necessary to make the injectable suspension isotonic.

According to another advantageous embodiment, the nanoparticles according to the invention are in the form of a lyophilisate.

As indicated above, the present invention is also directed toward the use of at least one nanoparticle according to the invention in pharmaceutical compositions.

Another aspect of the invention therefore relates to a pharmaceutical composition comprising, as active material, at least one complex in accordance with the present invention, in particular in the form of nanoparticles. The complexes in accordance with the present invention may be combined therein with at least one pharmaceutically acceptable vehicle.

By way of examples of pharmaceutical formulations compatible with the compositions according to the invention, mention may in particular be made of intravenous injections or infusions;
saline solutions or solutions of purified water;
compositions for inhalation;
capsules, sugar-coated tablets, cachets and syrups incorporating in particular, as vehicle, water, calcium phosphate, sugars, such as lactose, dextrose or mannitol, talc, stearic acid, starch, sodium bicarbonate and/or gelatin.

When the complexes and/or nanoparticles are used as a dispersion in an aqueous solution, they may be combined with excipients such as sequestering or chelating agents, antioxidants, pH regulators and/or buffering agents.

In addition to the abovementioned compounds, the pharmaceutical compositions according to the invention may contain agents such as preservatives, wetting agents, solubilizing agents and colorants.

They may, however, contain other active agents of which it may be beneficial to take advantage from a therapeutic point of view, together with the effect of the statins.

By way of representation of these active materials that may be combined with the complexes and/or nanoparticles in accordance with the present invention, mention may in particular be made of active agents intended to reduce arterial hypertension, such as antihypertensives or hypotensives or else other compounds with hypolipemic activity. Included among these are diuretics, such as thiazide diuretics, loop diuretics, for instance furozemide, anti-aldosterones, or else β-blockers such as acebutolol, atenolol, betaxolol, bisoprolol, esmolol, metoprolol, nebivolol, nadolol, oxprenolol, propranolol, pindolol, sotalol, carvedilol, labetalol, levobunolol or timolol, converting enzyme inhibitors (ACEIs, CEIs), such as benazepril, captopril, cilazapril, enalapril, fosinopril, imidapril, lisinopril, moexipril, perindopril, quinapril, ramipril, spirapril or trandolapril, angiotensin II receptor antagonists, such as candesartan, candesartan cilexetil, eprosartan, irbesartan, losartan and its potassium salt, olmesartan, olmesartan medoxomil, telmisartan or valsartan, calcium blockers, such as amlodipine, gallopamil, verapamii, amlodipine, barnidipine, felodipine, isradipine, lacidipine, lercanidipine, nicardipine, nifedipine, nimodipine, nisoldipine, nitrendipine or diltiazem, central antihypertensives, alpha-stimulants, such as prazosine, terazosine, alfuzosine, doxazosine or tamsulosine, peripheral alpha-blockers and vasodilators.

Mention may also be made of other hypolipemic agents chosen from: fenofibrate, bezafibrate, cipofibrate, colestipol, ezetinaibe, tiadenol, gemfibrozil, polyunsaturated omega-3 fatty acids, omega-3 acid triglycerides, benfluorex, alpha-tocopherol (vitamin E) and colestyramine.

The complexes and/or nanoparticles in accordance with the present invention can be administered by any of the conventional routes. However, as specified above, given the small size of their particles, they can be administered intravenously in the form of an aqueous suspension and are therefore compatible with the vascular microcirculation.

For obvious reasons, the amounts of complex and/or nanoparticle according to the invention that can be used are capable of varying significantly according to the method of use and the route selected for their administration.

On the other hand, for topical administration, it is possible to envision formulating at least one complex and/or nanoparticle in accordance with the present invention in a proportion of from 0.1% to 10% by weight, or even more, relative to the total weight of the pharmaceutical formulation under consideration.

The examples which follow illustrate the present invention without, however, being limited thereto.

The infrared spectra are obtained by measurement on a pure solid or liquid using a Fourier spectrometer (Bruker Vector® 22 Fourier Transform spectrometer). Only the significant absorptions are noted. The optical rotations were measured using a Perkin-Elmer® 241 polarimeter, at a wavelength of 589 nm. The $^1H$ and $^{13}C$ NMR spectra were recorded using a Bruker ARX® 400 spectrometer (at 400 MHz and 100 MHz, respectively, for $^1H$ and $^{13}C$) or a Bruker Avance® 300 spectrometer (at 300 MHz and 75 MHz, respectively, for $^1H$ and $^{13}C$). The mass spectra were recorded using a Bruker Esquire-LC® instrument. The thin layer chromatography analysis was carried out on silica $60F_{254}$ plates (layer of 0.25 mm). The column chromatography was carried out on silica 60 gel (Merck, 230-400 mesh ASTM). All the reactions using compounds sensitive to air or to water were carried out under a nitrogen atmosphere.

PDI=Polydispersity Index.

EXAMPLE 1

Preparation of the
4-(N)-squalenoyl-6-epi-pravastatin (SQprava)
Complex

Step 1.1: (4E,8E,12E,16E)-4,8,13,17,21-Pentamethyldocosa-4,8,12,16,20-pentaen-1-ol Squalenic aldehyde is reduced to squalenol. To do this, 106 mg (0.9 equiv., 2.7 mmol) of sodium borohydride are added, at 0° C., in small portions, to 1.15 g (3 mmol) of squalenic aldehyde dissolved in 6 ml of ethanol. The mixture is stirred under a nitrogen atmosphere at ambient temperature for 15 min, and then the reaction mixture is neutralized with a 2N solution of HCl. The solvent is then distilled off under reduced pressure. The residue is dissolved in 10 ml of water and extracted with ethyl acetate (3 times 20 ml) and the combined organic phases are washed with a saturated aqueous solution of NaCl (10 ml) and dried over $MgSO_4$, and then the solvent is distilled off under reduced pressure, to give a pale yellow oil.

IR (pure, $cm^{-1}$) ν: 3060-2840, 1667 (weak), 1445, 1381.
$^1H$ NMR (300 MHz, $CDCl_3$) δ: 5.16-5.09 (m, 5H), 3.62 (t, J=6.4, 2H), 2.13-1.94 (m, 21H), 1.61 (s, 3H), 1.53 (s, 15H).
MS (APCI+, MeOH), m/z (%): 387 ($[M+H]^+$ (100)).

Step 1.2: (4E,8E,12E,16E)-4,8,13,17,21-pentamethyldocosa-4,8,12,6,20-pentaen-1-yl bromoacetate 216 mg (1.55 equiv., 2.01 mmol) of bromoacetic acid and a few mg of DMAP are added to 500 mg (1.3 mmol) of squalenol dissolved in 6 ml of anhydrous $CH_2Cl_2$. The mixture is cooled to 0° C. and then 317 mg (1.5 equiv., 1.95 mmol) of DCC dissolved in 2 ml of $CH_2Cl_2$ are added in small portions. After the addition is complete, the mixture is stirred under a nitrogen atmosphere at ambient temperature for 18 h and then filtered through celite. The filtrate is concentrated under reduced pressure. The residue is chromatographed on silica gel using an EtOAc/cyclohexane mixture: 1/4, to give 55 mg of a colorless oil.

IR (pure, cm$^{-1}$) v: 2960-2850, 1737, 1668 (weak), 1450, 1382, 1276, 1381.

$^1$H NMR (300 MHz, CDCl$_3$) δ: 5.18-5.07 (m, 5H), 4.14 (t, J=6.4, 2H), 3.82 (s, 2H), 2.16-1.98 (m, 18H), 1.81-1.71 (m, 2H), 1.68 (s, 3H), 1.53 (s, 15H); $^{13}$C (75 MHz, CDCl$_3$) δ: 167.2 (C), 135.0 (C), 134.8 (2C), 133.2 (C), 131.2 (C), 125.3 (CH), 124.4 (2CH), 124.2 (2CH), 65.9 (CH$_2$), 39.7 (2CH$_2$), 39.6 (CH$_2$), 35.5 (CH$_2$), 28.2 (2CH$_2$), 28.7 (CH$_2$), 26.6 (CH$_2$), 26.5 (2CH$_2$), 25.6 (CH$_2$), 25.6 (CH$_3$), 17.6 (CH$_3$), 16.0 (3CH$_3$), 15.8 (CH$_3$).

Step 1.3: 2-Oxo-2-{[(4E,8E,12E,16E)-4,8,13,17,21-pentamethyldocosa-4,8,12,16,20-pentaen-1-yl]oxy}ethyl (3R,5R)-3,5-dihydroxy-7-((1S,2S,6R,8S,8aR)-6-hydroxy-2-methyl-8-{[(2S)-2-methylmutanoyl]oxy}-1,2,6,7,8,8a-hexahydronaphthalen-1-yl)heptanoate 111 mg (2 equiv., 0.22 mmol) of squalenyl bromoacetate are added to 50 mg (0.11 mmol) of 6-epi-pravastatin dissolved in 0.4 ml of anhydrous DMSO. The mixture is heated, under a nitrogen atmosphere, at 40° C. for 5 h and then the solvent is distilled under reduced pressure. The residue is chromatographed on silica gel using an EtOAc/cyclohexane mixture: 1/1, to give 55 mg of pravastatin-SQ in the form of an amorphous white solid.

[α]$_D$=77.7 (c=2.4, CHCl$_3$);

IR (pure, cm$^{-1}$) v: 3500-3200, 2924, 1728, 1448, 1375, 1264, 1182, 1151.

$^1$H NMR (CDCl$_3$, 400 MHz) δ: 5.99 (d, J=9.7 Hz, 1H, H-4), 5.89 (dd, J=9.7; 6.0 Hz, 1H, H-3), 5.56 (s, 1H, H-5), 5.42 (s, 1H, H-8), 5.20-5.05 (m, 5H, HC=C(Me)), 4.72 (d, J=15.8 Hz, 1H, OCH$_2$OCO), 4.61 (d, J=15.8 Hz, 1H, OCH$_2$OCO), 4.46-4.36 (m, 1H, H-6), 4.38-4.22 (m, 1H, H-3'), 4.15 (t, J=6.9 Hz, 2H, OCH$_2$CH$_2$CH$_2$C(Me)), 3.91 (broad s, 1H, OH), 3.83-3.78 (m, 1H, H-5'), 3.53 (broad a, 1H, OH), 2.65-2.55 (m, 3H, 2H-2', H-1), 2.46-2.35 (m, 1H, H-2), 2.35-2.28 (m, 2H, HC(Me)(Et)CO$_2$), 2.12-1.92 (m, 18H, =C(Me)CH$_2$CH$_2$), 1.75 (quint, J=8.0 Hz, 2H, OCH$_2$CH$_2$CH$_2$C(Me)), 1.68 (s, 3H, =C(CH$_3$)$_2$), 1.69-1.50 (m, 21H, 5=C(CH$_3$), H-7, H-4', 1H CH$_3$CH$_2$CH(Me)CO$_2$, 1H 6'), 1.49-1.35 (m, 2H, 1H CH$_3$CH$_2$CH(Me)CO$_2$, 1H-7'), 1.16 (m, 1H, 1H-6'), 1.11 (d, J=6.8 Hz, 3H, (CH$_3$)(Et)CHCO$_2$), 0.90 (d, J=7.6 Hz, 3H, C-2(CH$_3$)), 0.88 (d, J=7.6 Hz, 3H, (CH$_3$)(CH$_2$CH$_3$)CHCO$_2$);

$^{13}$C NMR (CDCl$_3$, 100 MHz) δ: 176.3 (CO), 171.3 (CO), 168.3 (CO), 136.1 (CH), 135.6 (C), 135.1 (C), 134.9 (2C), 133.3 (C), 131.2 (C), 127.3 (CH), 125.9 (CH), 125.4 (CH), 124.4 (2CH), 124.3 (2CH), 72.2 (CH), 69.5 (CH), 69.2 (CH), 65.6 (CH$_2$), 65.1 (CH), 60.6 (CH$_2$), 42.35 (CH$_2$), 42.30 (CH$_2$), 41.6 (CH), 39.7 (CH$_2$), 39.6 (CH$_2$), 37.7 (CH), 36.8 (CH$_2$), 36.6 (CH), 35.6 (CH$_2$), 34.6 (CH$_2$), 30.9 (CH), 28.3 (2CH$_2$), 26.8 (CH$_2$), 26.65 (3CH$_2$), 26.60 (2CH$_2$), 25.7 (CH$_3$), 23.8 (CH$_2$), 16.8 (CH$_3$), 16.0 (4CH$_3$), 15.8 (CH$_3$), 13.6 (CH$_3$), 11.8 (CH$_3$);

MS (ESI+, MeOH, DMSO), m/z (%): 874 ([M±Na]$^+$ (100)).

EXAMPLE 2

Preparation of Pravastatin Nanoparticles

Preparation of Nanoparticles Consisting of 4-(N)-squalenoyl-6-epi-pravastatin

The nanoparticles are obtained by means of the precipitation/solvent evaporation method, by analogy with the method described in Fessi H. et al, Int. J. Pharm, 55; 1989, R1-R4.

4 mg of SQpravastatin are dissolved in 0.5 ml of ethanol in a pill bottle. In another flask, 2 mg of SQ-PEG are dissolved in 0.2 ml of acetone and 0.1 ml of ethanol, in the order mentioned. The two solutions are then mixed and the solution obtained is added dropwise, with stirring (500 rpm), to 1 ml of a 5% aqueous solution of dextrose. The nanoparticles precipitate immediately. The bottle contained the SQpravastatin solution is rinsed and the rinsing solution is added to the suspension of nanoparticles. After 2 or 3 minutes of stirring, the suspension of nanoparticles is transferred into a tared round-bottomed flask and concentrated under reduced pressure in a rotary evaporator (50-100 mbar at 20° C. for 10 min and then at 37° C. for approximately 3-5 minutes) until a weight of 0.8-0.9 g is obtained. The solution is then made up to 1 g using either a 5% dextrose solution or sterile water. The size of the nanoparticles obtained, measured with a Malvern nanosizer (Zetasizer), is 146 nm.

The nanoparticles have a mean size compatible with any mode of administration, and also good stability in an aqueous solution.

They have a polydispersity index of 0.08.

The polydispersity index was determined according to methods well known to those skilled in the art (for example, by analogy with the method described in Couvreur et al., Nanoletters, vol. 6, No. 11, pages 2544-2548, 2006).

The invention claimed is:

1. A complex made up of (i) at least one molecule of statin or a derivative thereof, said molecule comprising a 4-hydroxy-6-oxo-2H-pyran system or a dihydroxy acid form thereof, and a lipophilic part presenting an aryl, an heteroaryl or a 1,2,6,7,8,8a-hexahydronaphtyl group, optionally substituted, and said molecule being covalently coupled to (ii) at least one hydrocarbon-based radical comprising at least 18 carbon atoms and containing at least one unit represented by the formula which follows:

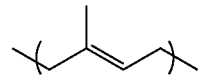

2. The complex of claim 1, in which the hydrocarbon-based compound comprises from 18 to 40 carbon atoms.

3. The complex of claim 1, in which the hydrocarbon-based radical is represented by the radical of formula (I) which follows:

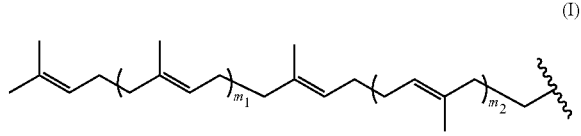
(I)

in which:
m$_1$=1, 2, 3, 4, 5 or 6;
m$_2$=0, 1, 2, 3, 4, 5 or 6; and

represents the bond toward the molecule of statin or a derivative thereof, it being understood that, when $m_2$ represents 0, then $m_1$ represents at least 2.

4. The complex of claim 1, in which the hydrocarbon-based radical is represented by the radical of formula (I)

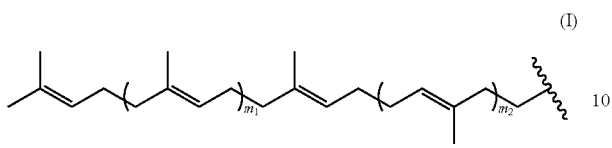

in which:
$m_1$ represents 1;
$m_2$ represents 2; and

represents a bond toward the molecule of statin or a derivative thereof.

5. The complex of claim 1, in which the lipophilic part presents a polysubstituted hexahydronaphthalenic or polysubstituted heteroaromatic system.

6. The complex of claim 1, in which the molecule, derived from a statin, is represented by formula (IIa), (IIb) or (IIc) which follows:

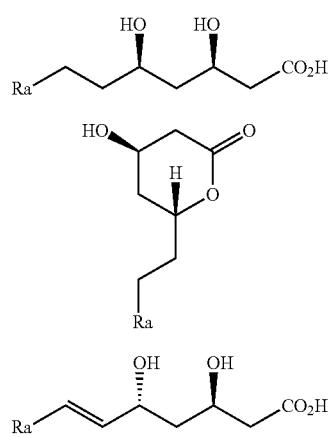

in which:
$R_a$ represents an aryl or heteroaryl group, optionally substituted with one or more R group(s);
R independently represents a hydroxyl group, a $C_1$-$C_6$ alkyl group, a $C_1$-$C_6$ alkoxy group, an —O—C(O)$C_1$-$C_6$ alkyl group, a phenyl, an —NR$_1$R$_2$ group, a —C(O)NR$_1$R$_2$ group or a —C(O)OR$_3$ group, said alkyl and phenyl groups being optionally substituted with one or more halogen atoms or with one or more hydroxyl groups;

R$_1$ and R$_2$ represent, independently of one another, a hydrogen atom, a $C_1$-$C_6$ alkyl group, an —SO$_2$—$C_1$-$C_6$ alkyl or a phenyl, said $C_1$-$C_6$ alkyl and phenyl groups being optionally substituted with one or more halogen atoms or with one or more hydroxyl groups;

R$_3$ represents a hydrogen atom, or a $C_1$-$C_6$ alkyl optionally substituted with one or more halogen atoms or with one or more hydroxyl groups;

in the form of a base or of an addition salt with an acid, and also in the form of a hydrate or of a solvate, and also its enantiomers and diastereoisomers, and a mixture thereof.

7. The complex of claim 1, in which the molecule, derived from a statin, is chosen from atorvastin, lovastatin, simvastatin, pravastatin, fluvastatin and rosuvastatin.

8. The complex of claim 1, in which the two entities forming said complex are coupled by means of a covalent bond of ester, ether, thioether, disulfide, phosphate or amide type.

9. The complex of claim 1, represented by the compound of formula (III) which follows:

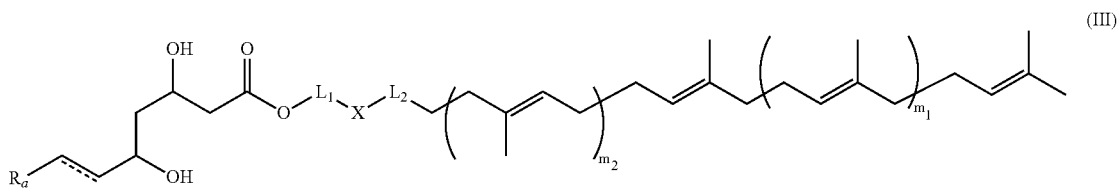

in which:
X represents a single covalent bond or a function of ester, ether, thioether, disulfide, phosphate or amide type;
$L_1$ and $L_2$ represent, independently of one another, a single covalent bond or a $C_1$-$C_4$ alkylene group; and
$R_a$ is as defined for the compound of formula (IIa), (IIb) or (IIc); and $m_1$ and $m_2$ are as defined for the compound of formula (I); and represents the optional presence of a center of unsaturation, in the form of a base or of an addition salt with an acid, and also in the form of a hydrate or of a solvate, and also its enantiomers and diastereoisomers, and a mixture thereof.

10. The complex of claim 1, characterized in that it has the ability to organize spontaneously in the form of nanoparticles when it is in the presence of an aqueous medium.

11. Nanoparticles of a complex as described according to claim 1.

12. The nanoparticles as claimed in claim 1, the mean size of which ranges from 30 to 500 nm.

13. The nanoparticles of claim 11, of 4-(N)-squalenoyl-6-epi-pravastatin.

14. A method for preparing nanoparticles, the method comprising:
the dispersion of a complex as claimed in claim 1, in at least one organic solvent, at a concentration sufficient to obtain, when the resulting mixture is added, with stirring, to an aqueous phase, the instantaneous formation of nanoparticles of said complex in suspension in said aqueous phase, and optionally, the isolation of said nanoparticles.

15. The preparation method of claim 14, also comprising a lyophilization step.

16. A lyophilisate comprising at least one complex as defined according to claim 1.

17. A pharmaceutical composition comprising at least one complex as defined according to claim 1, said complex being optionally in the form of a lyophilisate, in combination with at least one acceptable pharmaceutical vehicle.

* * * * *

UNITED STATES PATENT AND TRADEMARK OFFICE
CERTIFICATE OF CORRECTION

PATENT NO.         : 8,748,414 B2
APPLICATION NO.    : 13/126752
DATED              : June 10, 2014
INVENTOR(S)        : Patrick Couvreur et al.

It is certified that error appears in the above-identified patent and that said Letters Patent is hereby corrected as shown below:

On the title page, change Item (76) to Item (75)

On the title page, Column 1, please add Item (73) Assignees and under Item (73):

Please add
--Centre National de la Recherche Scientifique, Paris, France; Université Paris Sud, Orsay, France--

Signed and Sealed this
Sixteenth Day of September, 2014

Michelle K. Lee
*Deputy Director of the United States Patent and Trademark Office*